United States Patent [19]

Perry

[11] Patent Number: Plant 6,781

[45] Date of Patent: May 9, 1989

[54] ROSE PLANT NAMED PURE LOVE

[75] Inventor: Anthony Perry, Hemet, Calif.

[73] Assignee: Co-Operative Rose Growers, Inc., Tyler, Tex.

[21] Appl. No.: 103,740

[22] Filed: Oct. 2, 1987

[51] Int. Cl.[4] ..... A01H 5/00

[52] U.S. Cl. ..... Plt./14

[58] Field of Search ..... Plt. 14

*Primary Examiner*—Robert E. Bagwill
*Attorney, Agent, or Firm*—Vincent G. Gioia

[57] ABSTRACT

A new white hybrid tea rose.

1 Drawing Sheet

The present invention relates to a new and distinct variety of rose plant of the hybrid tea rose class, which was originated by my crossing as seed parent the variety known as "Queen Elizabeth" (U.S. Plant Pat. No. 1,259) and as pollen patent the rose known as "World Peace". The denomination of this new rose is "Pure Love".

Among the novel characteristics possessed by this new variety which distinguish it from its parents and all other varieties of which I am aware are its strong vigorous plant which attractively displays the abundantly produced white hybrid tea flowers that despite a tendency to sunburn at petal edges, maintain their color well upon aging. Asexual reproduction by budding of the new variety as performed in Smith County, Tex. shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "158D" is plate 158D of The Royal Horticultural Society Colour Chart.

Parentage: Seedling.
*Seed parent.*—"Queen Elizabeth".
*Pollen parent.*—"World Peace".
Class: Hybrid Tea.

The following observations are made of specimens grown outdoors in Smith County, Tex., during the month of June.

FLOWER

Blooming habit: Continuous.

A. Bud:
(1) *Size.*—Medium.
(2) *Form.*—Pointed.
(3) *Color.*—As sepals separate, bud color is near 158D.
(4) *Sepals.*—Pointed, slighly longer than bud.

(5) *Peduncle.*—Length — about 3 inches. Aspect — straight. Strength — erect. Color — near purplish green.

B. Bloom:
(1) *Size.*—Average size when fully expanded — about 4½ inches.
(2) *Borne.*—Singly, one to a stem.
(3) *Form.*—Globular, becoming cupped upon opening. Outer petals roll under.
(4) *Petalage.*—Number of petals under normal conditions — about 35 to 40.
(5) *Color.*—After sepals fall and petals unfurl, predominant flower color is white near 155D. Petal undersurface tends to near 158D with off white, cream coloring increasing toward point of petal attachment. As flowers age, sunburning appears at petal edges and overall tonality is between 155D and 158C.

C. Petals:
(1) *Texture.*—Average to thick.
(2) *Appearance.*—Outside satiny.
(3) *Form.*—Broad.
(4) *Arrangement.*—Regularly arranged.
(5) *Petaloids in center.*—Few.
(6) *Persistence.*—Average.
(7) *Fragrance.*—Slight.
(8) *Lasting quality.*—Average.

REPRODUCTIVE ORGANS

A. Stamens, filaments and anthers:
*Arrangement and color.*—Regularly arranged around styles Color — orange.

B. Pollen:
*Color.*—Yellow.

C. Styles: Medium length.

D. Stigmas:
*Color.*—Cream.

E. Hips: Globular shape, medium size, orange red color, seeds protrude slightly.

PLANT

A. Form: Tall, upright.

B. Growth: Vigorous, good branching.
*Height attained.*—about 5 feet.

C. Foliage: Compound 5 to 7 leaflets.
(1) *Size.*—Medium.
(2) *Quantity.*—Abundant.
(3) *Color.*—New foliage: purplish green. Old foliage: Upper side — near 137A. Under side — near to 137B.
(4) *Shape.*—Oval, pointed.

(5) *Texture.*—Upper side is leathery; under side is matte.

(6) *Edge.*—Serrate.

(7) *Serration.*—Ordinary.

(8) *Leaf stem.*—Color — light green, bownish tint.

(9) *Stipules.*—Medium length.

(10) *Resistance to disease.*—Blackspot — good. Mildew — good. Rust — good.

D. Wood:

(1) *New wood.*—Color — light green. Bark — smooth.

(2) *Old wood.*—Color — darker green. Bark — smooth.

E. Thorns:

(1) *Thorns.*—Quantity (main stalk) — ordinary. On laterals from stalk — average. Form — thin, slight recurve. Length — medium. Color — greenish brown. Position — irregular.

F. Winter hardiness: Needs protection in severe climates.

I claim:

1. A new and distinct variety of rose plant of the hybrid tea rose class, substantially as shown and described, characterized particularly by white flowers attractively displayed on a vigorous plant with dark green foliage.

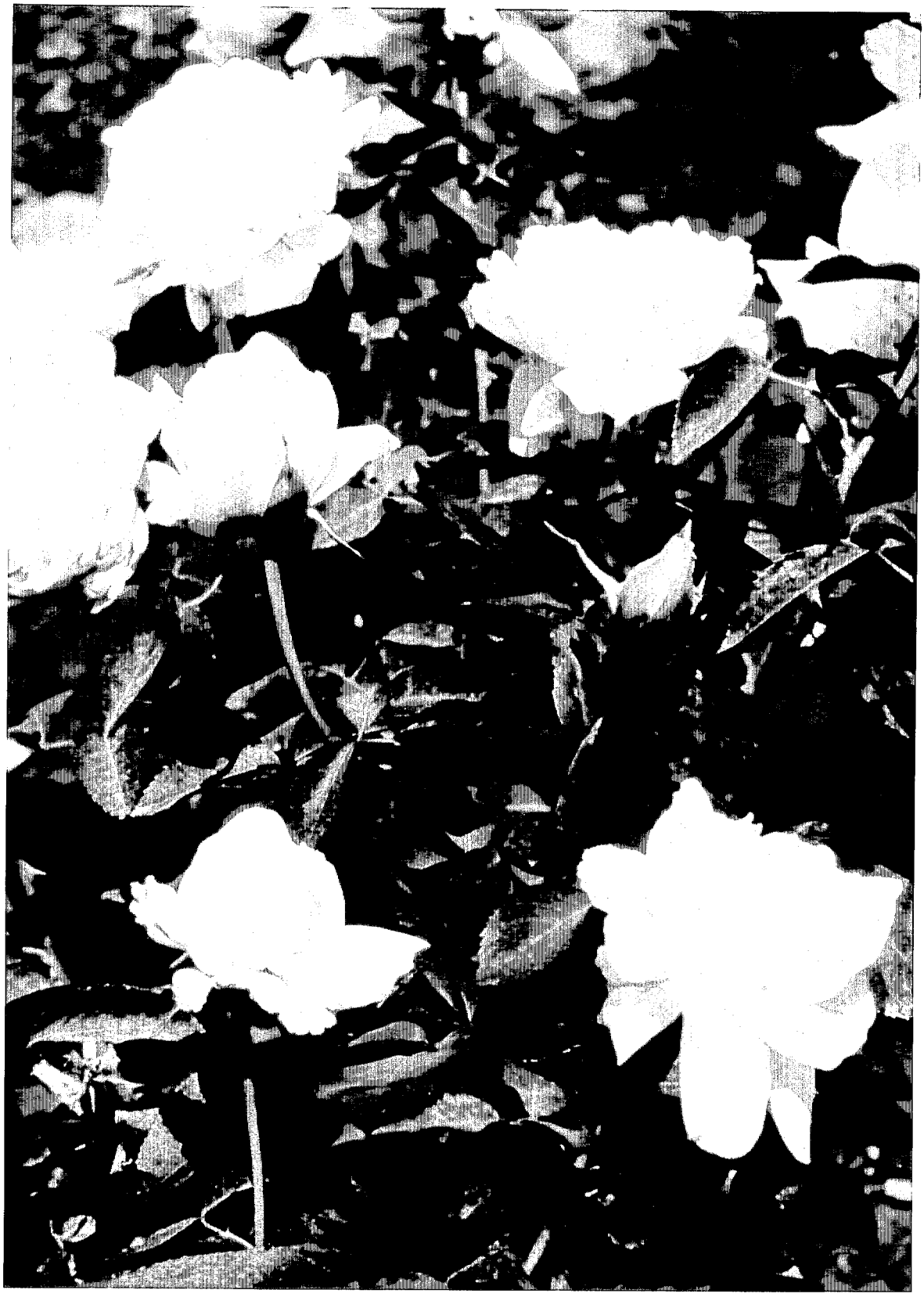

* * * * *